United States Patent [19]
Nelson

[11] Patent Number: 4,719,926
[45] Date of Patent: Jan. 19, 1988

[54] HINGED FOOT AND ANKLE BRACE

[76] Inventor: Ronald E. Nelson, 405 Sunset La., Cambridge, Minn. 55008

[21] Appl. No.: 834,595

[22] Filed: Feb. 28, 1986

[51] Int. Cl.⁴ .............................................. A61F 3/00
[52] U.S. Cl. .................... 128/80 H; 128/581; 36/89
[58] Field of Search ............... 128/80 H, 80 F, 80 E, 128/80 R, 88, 581, 166; 623/47; 36/89, 90, 120, 121

[56] References Cited

U.S. PATENT DOCUMENTS

| | | | |
|---|---|---|---|
| 260,069 | 6/1882 | Wallace | 36/89 |
| 325,280 | 9/1885 | Smadbeck et al. | |
| 332,727 | 12/1885 | McEwen | |
| 363,516 | 5/1887 | Hackey | |
| 605,299 | 6/1898 | Perrottet | |
| 654,286 | 7/1900 | Sears | 128/166 |
| 660,885 | 10/1900 | Braver et al. | 128/166 |
| 832,613 | 10/1906 | Krieger | |
| 851,950 | 4/1907 | LeMat | |
| 921,563 | 5/1909 | Quenzer | |
| 929,179 | 7/1927 | Wood | |
| 1,007,567 | 10/1911 | Holder | 128/88 |
| 1,037,441 | 9/1912 | Collis | |
| 1,081,366 | 12/1913 | Collis | |
| 1,084,197 | 1/1914 | Collis | |
| 1,383,928 | 7/1921 | Gassette | 128/88 |
| 1,708,757 | 4/1929 | Freileweh | 128/80 H X |
| 2,994,322 | 8/1961 | Cullen et al. | |
| 3,067,531 | 12/1962 | Scott et al. | 128/581 X |
| 3,073,305 | 1/1963 | Biggs, Jr. et al. | |
| 3,298,365 | 1/1967 | Lewis | |
| 3,779,654 | 12/1973 | Horne | 128/80 H X |
| 3,844,055 | 10/1974 | Koyama et al. | 36/120 |
| 4,237,874 | 12/1980 | Nelson | |
| 4,495,942 | 1/1985 | Palumbo | 128/80 H |
| 4,527,556 | 7/1985 | Nelson | 128/80 H |

FOREIGN PATENT DOCUMENTS

| | | | |
|---|---|---|---|
| 722436 | 7/1942 | Fed. Rep. of Germany | 36/121 |
| 1253682 | 1/1961 | France | 36/120 |

Primary Examiner—Clifford D. Crowder
Attorney, Agent, or Firm—L. Paul Burd; Richard O. Bartz; Robert W. Gutenkauf

[57] ABSTRACT

An ankle brace for constraining movement of the lower leg and foot about the normal horizontal axis of rotation of the ankle while inhibiting other rotation or extension or retraction movement about abnormal axes or in abnormal directions in order to help prevent injury to the ankle joint. The device includes a U-shaped leg member positionable in straddling relationship to the ankle joint and fixable to the lower leg. An ankle member is connected by a sliding pivot to the U-shaped leg member and is engaged with respect to the foot to hold the foot and lower leg together for movement about an arcuate path described by the sliding pivot joint.

4 Claims, 7 Drawing Figures

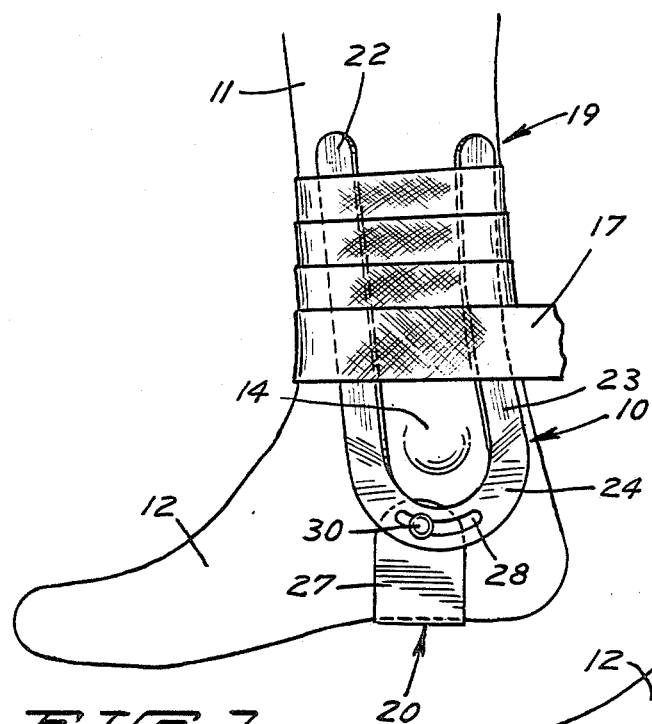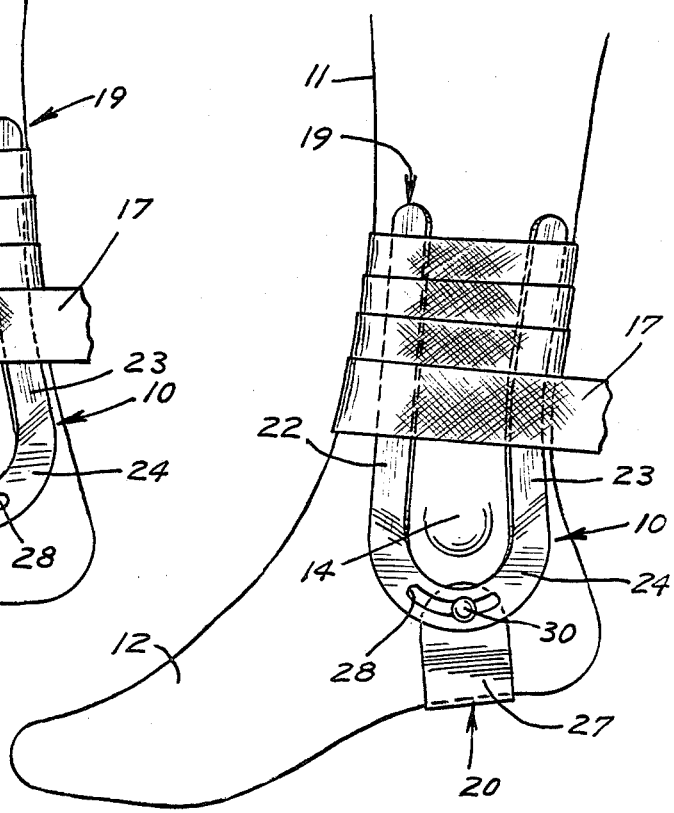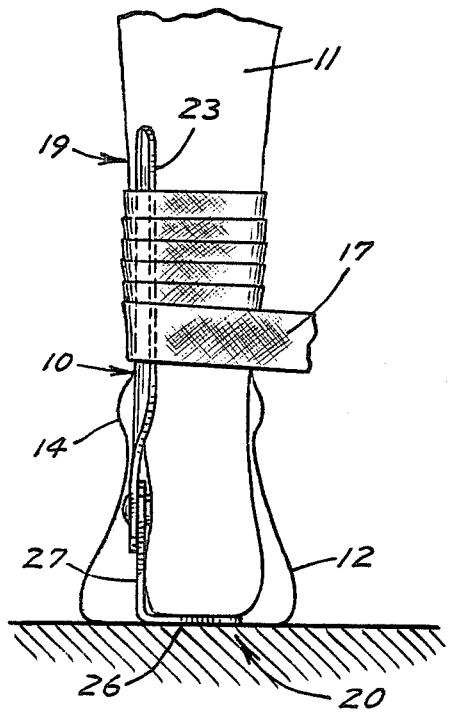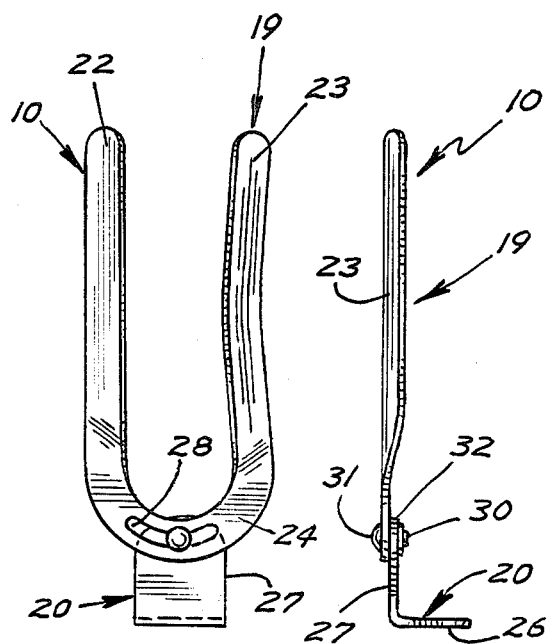

HINGED FOOT AND ANKLE BRACE

BACKGROUND OF THE INVENTION

The ankle joint is meant only to move up and down (dorsiflexion and plantar flexion). It is the complex articulation point of the fibula and tibia with the ankle bone and tarsal bones. It is not meant to rotate side to side, nor tilt inward or outward, and is also one of the most used and abused joints, particularly in the field of sports. Injury is caused or aggravated by inversion and eversion of the ankle joint, as well as twisting, hyperextension and the like resulting from awkward displacement of the foot from the lower leg. In mild versions of injury, the ankle bone is momentarily displaced and ligaments are stretched. Accordingly, various forms of gear are available to support and protect the ankle joint and deter it from movement in unintended direction. This includes tape, elastic wrap and braces of various types. While providing good support, such prior art devices are prone to unduly inhibit normal flexure between the foot and ankle.

SUMMARY OF THE INVENTION

The invention pertains to an ankle brace device having two articulated members, one secured relative to the foot and the other relative to the leg in order to hold the leg and foot in relative position and permit normal movement. The members are articulated for rotational movement about an axis generally corresponding to the normal horizontal axis of rotation between the leg and the foot or that of the ankle. The device can be mounted directly to the foot and leg, or it can be mounted integrally in footwear apparel, such as a boot. The ankle or leg member is U-shaped having first and second resiliently flexible arms disposable in straddling relationship to the lateral malleolus. A curved shoulder connects the arms and extends arcuately beneath the lateral malleolus or outside ankle joint. The shoulder has an arcuate slot that describes an arc formed about a center which generally coincides with the normal pivot axis of the ankle joint. In secured relationship to the ankle, the arms and accompanying wrap or shoe, support and limit lateral flexure of the ankle and inhibit forward and rearward extension, which might otherwise cause displacement of the ankle bone.

The anchor or foot member is generally L-shaped with a base engageable with a bottom portion of the foot proximate the juncture of the heel and instep and generally beneath the ankle joint when the ankle is in an upright orientation. An upright wall is connected to the base of the foot member and is disposed in a vertical plane along the outer side of the foot. It carries a pivot pin that slides in the arcuate slot of the leg member. The foot and leg members together substantially stabilize the location of the pivotal axis of rotation between the foot and the leg and prevent undue extension and rotation of the foot relative to the ankle and lower leg.

IN THE DRAWINGS

FIG. 1 is a side elevational view of an ankle brace device of the invention installed on a foot with the foot in a retracted position with respect to the leg;

FIG. 2 is a side elevational view of the ankle brace device of FIG. 1 with the foot in an extended position relative to the leg;

FIG. 3 is a rear elevational view of the ankle brace device of FIG. 1 installed on a foot;

FIG. 4 is a side elevational view of the ankle brace device;

FIG. 5 is an end view of the ankle brace device of FIG. 4;

DESCRIPTION OF PREFERRED EMBODIMENTS

Figure 6:
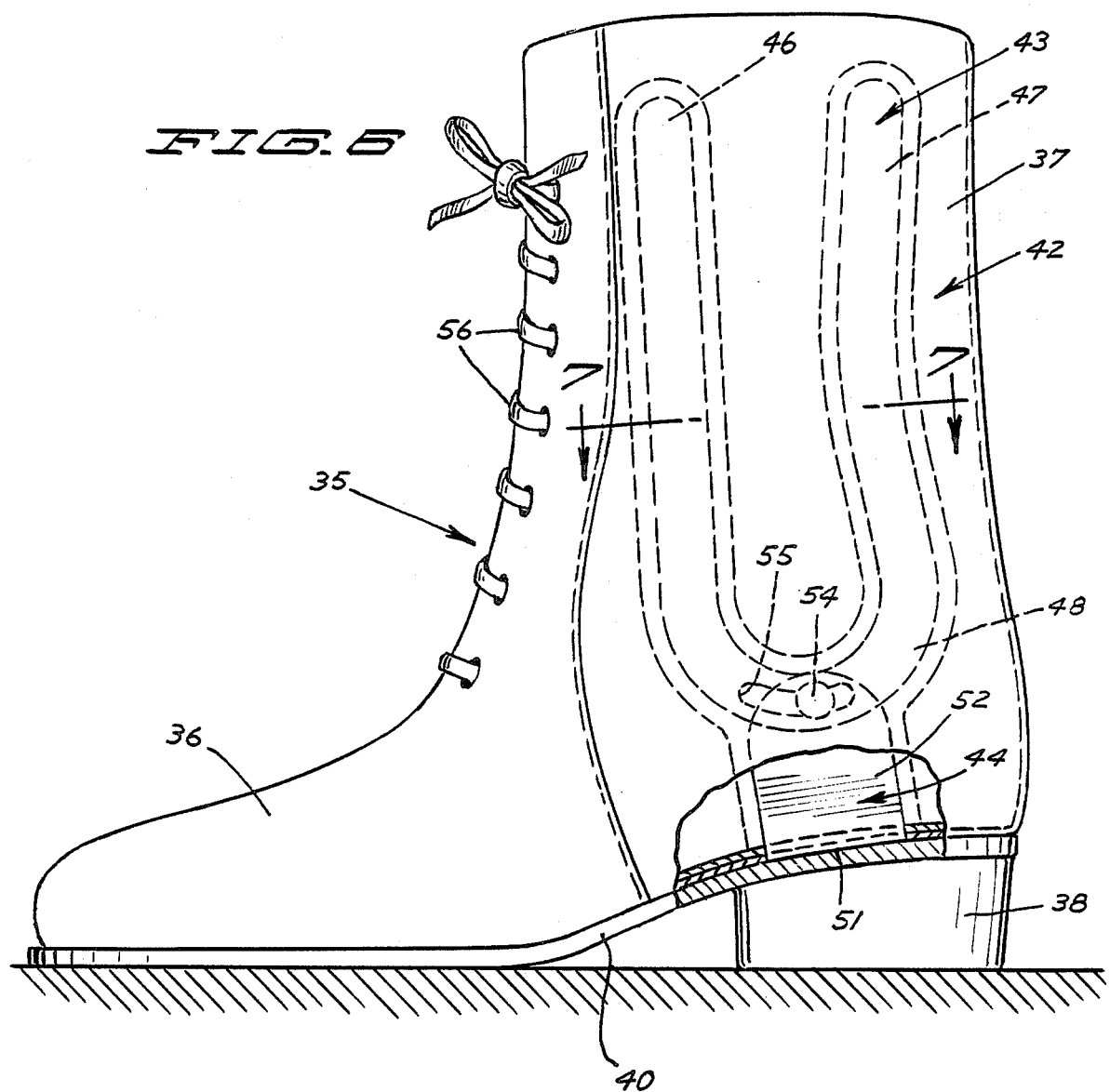
FIG. 6 is a side elevational view of a piece of footwear apparel having an ankle brace device according to the invention installed therein.

Referring to the drawings, there is shown in FIGS. 1 through 3, an ankle brace device indicated generally at 10 installed on the lower leg 11 and foot 12 of a wearer in spanning and protective relationship to the lateral malleolus or outer ankle joint 14. Device 10 inhibits inversion and eversion of the ankle joint, twisting, and other rotation about an abnormal axis removed from the normal horizontal axis of rotation of ankle 14. Device 10 can be used in conjunction with an ankle wrap 17 and permits normal flexure or rotation of the foot with respect to the lower leg about the ankle joint while tending to hold the foot and lower leg in proper alignment.

As shown in FIGS. 1-3, the device 10 is installed directly on the left foot of the user. In the view of FIG. 1, the foot is rotated slightly upward or in dorsiflexion. In the view of FIG. 2, the foot is slightly extended or in plantar flexion. The ankle brace 10 permits rotation between the two positions while providing stability to the ankle joint against inversion, eversion or the like movement tending to displace the foot from the lower leg.

Device 10 includes a leg member 19 pivotally connected by a sliding pivot connection to a foot or anchor member 20. Leg member 19 is generally U-shaped and has first and second upwardly extended, spaced apart, and generally parallel stay members or arms 22 and 23 that are connected at their lower ends by an arcuate shoulder 24. As properly fitted on the leg and foot, the lower ends of arms 22, 23 straddle the lateral malleolus 14. The shoulder 24 curves downwardly around it. The upper ends of arms 22, 23 extend along the lower leg to a location well above the ankle region. Leg member 19 is formed of a relatively stiff metallic or like material, such that arms 22 and 23 have a limited measure of resilient lateral flexure but are longitudinally rigid. As shown in FIGS. 4 and 5, the shoulder 24 is generally flat, and arms 22, 23 can twist slightly inward so as to better conform as to the surface of the leg areas which they engage. Leg wrap 17 wraps around the lower leg and the upper ends of the arms 22 and 23 to closely hold leg member 19 in contact with the lower leg portion and longitudinally and laterally fixed with respect to it.

Anchor or foot member 20 is L-shaped to generally conform to a side and bottom portion of the foot. A first portion or base 26 is positionable in engagement with the bottom of the foot proximate the juncture of the heel and the instep at a location generally beneath the lateral malleolus. A second portion or upright wall 27 is in complementary relationship to the base 26 and extends vertically upward along the side of the foot to the vicinity of shoulder 24. Shoulder 24 has an arcuate track or slot 28. Slot 28 describes an arc or circular segment having a center approximately coincidental with the normal horizontal axis of rotation of the ankle when the leg member 19 is properly fitted on the leg and ankle. The wall 27 of the foot member 20 carries a pivot pin 30 that rides in slot 28. Pin 30 has a head 31 and a lock washer 32 disposed on opposite sides of the slot 28. Anchor member 20 is rotatably connected to the leg member 19 and movably connected to it for movement along the slot 28. Pivot pin 30 rides in and follows slot 28, such that the anchor member 20 is movable with respect to the leg member 19 about an arc having a center that is generally coincidental with the axis of rotation of the ankle joint. This permits relative rotational movement of the anchor member 20 and, accordingly, the foot 12 about the ankle joint 14 with respect to the lower leg 11 while maintaining proper relationship between the foot, ankle and lower leg.

In use, ankle brace 10 is installed on the foot 12 and lower leg 11 of the user, preferably on the outside thereof, so that the shoulder 24 and lower portions of the arms 22 and 23 of the leg member 19 straddle the lateral malleolus. In this position, the base 26 of the foot member 20 is held in snug engagement with the undersurface of the foot proximate the intersection of the instep and the heel. The ankle wrap 17 is wrapped around the lower leg and the arms 22, 23 of leg member 19 to firmly hold the brace 10 in place with respect to the foot and give a measure of protection itself. In this configuration, the arms 22, 23 of the leg member 19 are effective to inhibit twisting of the leg and foot in the vicinity of the ankle. However, the pivot pin 30 riding in the slot 28 permits normal flexure of the foot with respect to the ankle and lower leg. The lower leg, ankle and foot are held together by the connection between the leg and anchor members. The slight twist configured in the legs 22, 23 permits close conformance to the lower leg 11 (see FIG. 3). If desired, additional warp or protection can be applied to the foot and ankle. The foot can readily be fitted in a normal shoe or other athletic footwear, such as an ice skate, football shoe, or ski boot.

Figure 7:
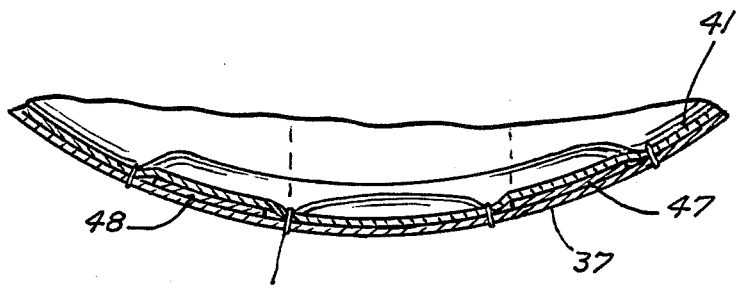
FIG. 7 is an enlarged sectional view of a portion of the footwear apparel of FIG. 6 taken along the line 7—7 thereof.

According to the form of the invention shown in FIGS. 6 and 7, there is provided an item of footwear shown as a boot 35 having a vamp 36, flexible side 37, heel 38 and sole 40. A liner 41 is fixed to the inner portion of the side 37 for purposes of comfort. An ankle brace 42 according to the invention is installed in the side 37 of boot 35 and includes a leg member 43 and a foot or anchor member 44. Leg member 43 is generally U-shaped having upwardly extended, spaced apart and somewhat parallel arms 46, 47 and an arcuate shoulder 48 connecting the lower ends of the arms. The leg member 43 is accommodated in suitable pockets formed between the liner 41 and the side 37 as by stitching 50. The foot member 44 has a flat base 51 that extends parallel to the sole 40 for intended disposition beneath the heel of the foot of the wearer. Base 51 is fixed to the inside surface of the sole 40. A wall 52 extends upward in complementary relationship to the base 51, along the side 37 of the boot 35 to the vicinity of shoulder 48. Wall 52 carries a pivot pin 54. The shoulder 48 of leg member 43 has an arcuate track or slot 55, which is formed along an arc having a center approximately coincidental with the pivotal axis of the ankle of the foot of a wearer when positioned in the boot 35. Pivot pin 54 rides in the slot 55. The pivot pin 54 and slot 55 permit rotational movement of a foot installed in the boot 35 with respect to the lower leg about the normal ankle joint. However, the arms 46, 47 are held in secure engagement against the leg, as by usual shoe laces 56, to inhibit inversion and eversion of the leg or abnormal twisting either about an upright axis or a forwardly extended horizontal axis.

In use, boot 35 is simply placed on the foot and leg of the wearer in normal fashion. Laces, snaps, support straps, or the like, are used in the usual fashion in order to tighten the boot with respect to the shoe and, particularly, the upper portion thereof comprising the side 37 so that the arms 46, 47 will be snugly in engagement with the lower leg of the user and base 51 anchored with respect to the foot.

While there have been shown and described certain embodiments of the invention, it will be apparent that certain deviations can be had without departing from the scope and spirit of the invention.

The embodiments of the invention in which an exclusive property or privilege is claimed are defined as follows:

1. An ankle brace device comprising:
   a generally U-shaped leg member for engagement of a leg, having first and second elongate arms positionable in vertically straddling relationship to the malleolus of the leg, and an arcuate shoulder connecting the lower ends of the arms and spaced beneath the malleolus when the arms are positioned in straddling relationship to the malleolus, said shoulder having a first hinge means comprised as an arcuate slot discribed about a center approximately coincidental with the horizontal axis of rotation of the hinge;
   means for fixing the leg member to a leg comprised as an elongate leg wrap for circumferentially wrapping around the leg and the first and second arms of the leg member to hold the leg member stationary with respect to the leg;
   an L-shaped anchor member having a base engagable with a bottom portion of the foot, and a side wall perpendicular to the base and positionable abutting the side of the foot, said side wall carrying a second hinge means comprised as a pivot pin engaged in the slot of the shoulder of the leg member to ride in the slot upon pivotal movement of the foot following the leg engaged by the leg member.

2. The ankle brace device of claim 1 wherein: said first and second arms of the leg member are formed of resiliently flexible material and are twisted slightly inward to more closely conform to the surface of the lower leg proximate the ankle.

3. An article of footwear for stabilizing a lower leg, ankle and foot for rotation of the ankle joint about its normal horizontal axis, comprising;
   a footwear upper having a flexible side and adapted to be worn around the lower leg and ankle;
   a generally U-shaped leg member having first and second upright elongate arms and an arcuate shoulder connecting the lower ends of the arms, said leg member fixed to the footwear upper in position for the first and second arms to be in straddling relationship to the lateral malleolus of the leg and extending upward of the leg beyond the ankle joint;
   arcuate slot means on the leg member describing a circular segment having a center generally coincidental with the normal horizontal axis of rotation of the ankle joint of a leg engaged by the footwear upper;
   a footwear lower having a sole fixed to the footwear upper adapted to engage the lower portion of the foot;

an L-shaped anchor member fixed to the sole configured to abut a lower portion and a side portion of a foot and leg engaged by the footwear upper, said anchor member having pin means connected to the slot means and riding in the slot means, said pin means slidable therein along the arc described by the slot means upon relative movement of the leg engaged by the footwear upper and the foot engaged by the anchor member.

4. The ankle brace device of claim 3 wherein: said first and second arms of the leg member are inwardly twisted in order to more closely conform to the surface of a lower leg.

* * * * *